United States Patent
Kondo et al.

(10) Patent No.: US 8,707,801 B2
(45) Date of Patent: Apr. 29, 2014

(54) TWO-PHASE FLOW EXCITING FORCE EVALUATION METHOD AND DEVICE ACTING ON A PLURALITY OF TUBE BODIES ARRANGED TO INTERSECT WITH THE FLOW

(75) Inventors: Yoshiyuki Kondo, Takasago (JP); Kenji Nishida, Kobe (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 357 days.

(21) Appl. No.: 13/133,807

(22) PCT Filed: Dec. 17, 2009

(86) PCT No.: PCT/JP2009/006990
§ 371 (c)(1),
(2), (4) Date: Jun. 9, 2011

(87) PCT Pub. No.: WO2010/134148
PCT Pub. Date: Nov. 25, 2010

(65) Prior Publication Data
US 2011/0239779 A1 Oct. 6, 2011

(30) Foreign Application Priority Data

May 19, 2009 (JP) .................................. 2009-121190

(51) Int. Cl.
*G01F 1/20* (2006.01)
(52) U.S. Cl.
USPC ...................................................... 73/861.18
(58) Field of Classification Search
None
See application file for complete search history.

(56) References Cited

FOREIGN PATENT DOCUMENTS

| JP | 62-56825 A | 3/1987 |
| JP | 5-46883 A | 2/1993 |
| JP | 2001-272494 A | 10/2001 |
| JP | 2007-33062 A | 2/2007 |

OTHER PUBLICATIONS

N. Yamaguchi et al., "Study on Two-Phase Flow Behavior and Turbulent Excitation Mechanism in a U-Ben Tube-Bundle in Steam Generators Based on Air-Water Two-Phase Flow Model Tests", JSME International Journal Series B, 1993, vol. 36, No. 3, pp. 439-448.
K. Kawamura et al., "Turbulence-Induced Tube Vibration by Parallel Air-Water Two-Phase Jet Flow", Transactions of the Japan Society of Mechanical Engineers (Series C), vol. 64, No. 627, 1998, pp. 4123-4131.
International Search Report of PCT/JP2009/006990, mailing date Jan. 26, 2010.
Written Opinion of PCT/JP2009/006990, mailing date Jan. 26, 2010.

*Primary Examiner* — Harshad R Patel
(74) *Attorney, Agent, or Firm* — Westerman, Hattori, Daniels & Adrian, LLP

(57) ABSTRACT

In a two-phase flow exciting force evaluation method of the present invention, the surface of one of a plurality of tube bodies (3) is at least partially formed from a conductive material, displacement or stress of the tube body (3) is measured in a state of being vibrated by a shaking device (4), and a void fraction of a two-phase flow (F) flowing in the vicinity of the tube body (3) is measured based on the potential difference between an electric potential at a predetermined position on the surface of the tube body (3), and a reference electric potential.

17 Claims, 5 Drawing Sheets

(a)

(b)

TWO-PHASE FLOW EXCITING FORCE EVALUATION METHOD AND DEVICE ACTING ON A PLURALITY OF TUBE BODIES ARRANGED TO INTERSECT WITH THE FLOW

TECHNICAL FIELD

The present invention relates to a two-phase flow exciting force evaluation method and a two-phase flow exciting force evaluation device for evaluating an exciting force which acts on a plurality of tube bodies arranged so as to intersect with the flow of a two-phase flow.

Priority is claimed on Japanese Patent Application No. 2009-121190, filed May 19, 2009, the contents of which are incorporated herein by reference.

BACKGROUND ART

For example, in a pressurized light-water reactor or an integrated modular light-water reactor, primary coolant in a pressurized state is circulated between a reactor core and a steam generator, and the heat of the primary coolant is transmitted to secondary coolant by the steam generator, to thereby generate steam. Here, inside the steam generator there are arranged a plurality of pipe lines bent in a U-shape and through which passes the primary coolant which circulates between the reactor core and the steam generator. By filling the surroundings of these pipe lines with the secondary coolant, the heat is transmitted from the primary coolant to the secondary coolant via the pipe lines, and this secondary coolant is evaporated, thereby generating steam. At this time, the U-shape pipe lines arranged inside the steam generator receive vibration from the primary coolant passing inside, and vibrate upon receiving an exciting force from the secondary coolant which is boiling and flowing as a two-phase flow.

Consequently, in the steam generator described above, a two-phase flow is flowed around the pipe lines on a trial basis to measure the void fraction of the two-phase flow, and the vibration characteristic of the vibrated pipe line is measured. Then, the exciting force which acts from the flowing two-phase flow on the pipe lines is associated with the void fraction and evaluated, and the pipe lines and members which fix these pipe lines are designed based on the results of this evaluation. Here, the void fraction of a two-phase flow can be found by arranging electrodes respectively on the inner surface and in the center portion of a flow path along which the two-phase flow travels, and measuring voltages occurring between these electrodes (for example, refer to Patent Document 1). Moreover, the vibration characteristic of the pipe line can be obtained by measuring a displacement occurring as a result of vibrations of the pipe line, using a displacement sensor, or by measuring stress occurring as a result of vibrations of the pipe line, using a stress sensor.

However, in the above evaluation of exciting force of two-phase flow, it is necessary to provide, independently in different positions, equipment that measures a two-phase flow void fraction on a flow path along which the two-phase flow travels, and equipment for vibrating the pipe line and measuring the vibrations thereof. Consequently, there is a problem in that the entire device including the flow path becomes large, and installation thereof is troublesome. Moreover, since each piece of equipment needs to be installed in different positions, there is a problem in that the measurement result of the measured two-phase flow void fraction and the measurement result of the vibration of the corresponding pipe line need to be synchronized, and it is difficult to make accurate measurements and measurement is time consuming.

PRIOR ART DOCUMENTS

Patent Documents

[Patent Document 1] Japanese Unexamined Patent Application, First Publication No. 2001-272494

DISCLOSURE OF INVENTION

Problems to be Solved by the Invention

The present invention takes into consideration the above circumstances, with an object of providing a two-phase flow exciting force evaluation method and a two-phase flow exciting force evaluation device capable, with a simple configuration, of easily and accurately evaluating an exciting force acting from a two-phase flow onto tube bodies.

Means for Solving the Problem

In order to solve the above problems, the present invention employs following measures.

The present invention is a two-phase flow exciting force evaluation method for evaluating an exciting force which acts, from a two-phase flow flowing in a flow section, on a plurality of tube bodies arranged so as to intersect with the flow of the two-phase flow. The two-phase flow exciting force evaluation method is characterized in that; the surface of one of the plurality of tube bodies is at least partially formed from a conductive material, displacement or stress of the tube body is measured in a state of being vibrated by a shaking device, and a void fraction of the two-phase flow flowing in the vicinity of the tube body is measured based on a potential difference between an electric potential at a predetermined position on the surface of the tube body, and a reference electric potential.

Moreover, the present invention is a two-phase flow exciting force evaluation device for evaluating an exciting force which acts, from a two-phase flow flowing in a flow section, on a plurality of tube bodies arranged so as to intersect with the flow of the two-phase flow. The two-phase flow exciting force evaluation device comprises: a vibration pipe which is configured as one of the plurality of tube bodies, and the surface of which is at least partially formed from a conductive material; a shaking device that vibrates the vibration pipe; an exciting force evaluating device that measures displacement or stress of the vibration pipe; and a void fraction measuring device that measures a void fraction of the two-phase flow flowing in the vicinity of the vibration pipe, based on a potential difference between an electric potential at a predetermined position on the surface of the vibration pipe, and a reference electric potential.

According to these method and configuration, the vibration pipe serving as one of the tube bodies arranged so as to intersect with the flow of the two-phase flow is vibrated by the shaking device, and it is excited by the exciting force acting as a reactive force of the vibration from the two-phase flow. The void fraction of the two-phase flow flowing in the vicinity in which an exciting force acts on the vibration pipe is measured based on a potential difference between an electric potential at a predetermined position on the surface of the vibration pipe, the surface of which is at least partially formed from a conductive material, and a reference electric potential. Furthermore, the exciting force which acts on the vibration pipe is evaluated by measuring a displacement or stress of the vibration pipe to be excited. Here, the void fraction of the two-phase flow and the exciting force acting on the pipe body can both be integrally measured without having to measure them respectively with independent equipment, by conducting measurement with use of the vibration pipe, the surface of which is at least partially formed from a conductive material. Therefore, installation of the device can be easily performed with a minimum number of members and a simple configuration without making the entire device large, and an exciting force and a void fraction can be associated with each other and can be accurately measured.

Furthermore it is preferable that in the above two-phase flow exciting force evaluation method, the velocity of the two-phase flow is further measured, and a critical velocity for each void fraction is found based on the void fraction and velocity of the measured two-phase flow and the displacement or stress of the tube body.

Moreover, it is preferable that in the above two-phase flow exciting force evaluating device, there is provided a two-phase flow velocity measuring device that measures the velocity of the two-phase flow.

Furthermore, it is preferable that in the above two-phase flow exciting force evaluating device, there is provided a critical velocity analyzing section that finds a critical velocity for each void fraction, based on the velocity of the two-phase flow measured by the two-phase flow velocity measuring device, the void fraction of the two-phase flow measured by the void fraction measuring device, and the displacement or stress of the vibration pipe measured by the exciting force evaluation device.

According to these method and configuration, the velocity of the two-phase flow is further measured. Accordingly, a critical velocity for each void fraction can be found based on the measured velocity and void fraction of the two-phase flow, and the displacement or stress of the vibration pipe.

Moreover, it is preferable that in the above two-phase flow exciting force evaluation method, the void fraction of the two-phase flow is found by measuring the potential difference between two points on the surface of the tube body.

Furthermore it is preferable that in the above two-phase flow exciting force evaluation device, the void fraction measuring device has a pair of first electrodes provided on the surface of the vibration pipe so as to have a clearance therebetween, a first voltage measuring section that detects a potential difference between the pair of first electrodes, and a void fraction analyzing section that calculates a void fraction based on the potential difference detected by the first voltage measuring section.

According to these method and configuration, the potential difference between the two points with a clearance therebetween on the surface of the vibration pipe changes according to the void fraction of the two-phase flow flowing in the vicinity thereof, and accordingly, a void fraction can be found by measuring the potential difference where one of the electric potentials is taken as a reference.

Furthermore, it is preferable that in the above two-phase flow exciting force evaluation method, on the surface of the tube body, a potential difference between another two points in positions which are different in the flow direction of the two-phase flow is further measured, and a local velocity of the two-phase flow flowing in the vicinity of the tube body is found based on a waveform phase difference of the potential difference measured respectively at both of the two points.

Moreover, it is preferable that in the above two-phase flow exciting force evaluation device, on the surface of the vibration pipe, at positions different in the flow direction of the two-phase flow from those of the pair of the first electrodes, there are provided a pair of second electrodes with a clearance therebetween, and there is provided a local velocity measuring device that includes the pair of first electrodes; the first voltage measuring section; the pair of second electrodes, a second voltage measuring section that detects a potential difference between the pair of second electrodes; and a local velocity analyzing section that finds the local velocity of the two-phase flow flowing in the vicinity of the vibration pipe, based on a waveform phase difference of the potential difference detected by the first voltage measuring section and a waveform phase difference of the potential difference detected by the second voltage measuring section.

According to these method and configuration, by measuring the potential difference respectively at the two points, changes in the void fraction can be measured as a waveform of the potential difference. Here, the pairs for measuring potential difference are respectively provided in positions different from each other in the flow direction of the two-phase flow, and therefore, the waveform of the potential difference is detected as having the phase displaced for the amount of displacement made in the flow direction of the two-phase flow. As a result, by measuring the waveform phase difference of the potential difference, the local velocity of the two-phase flow flowing in the vicinity of the vibration pipe can be found.

Furthermore, in the above two-phase flow exciting force evaluation method, the void fraction of the two-phase flow may be found by measuring the potential difference between the potential on the surface of the tube body and that on the inner surface of the flow section.

Moreover, in the above two-phase flow exciting force evaluation device, the void fraction measuring device may have an electrode provided on the inner surface of the flow section so as to face the surface of the vibration pipe, a voltage measuring section that detects a potential difference between the vibration pipe and the electrode, and a void fraction analyzing section that calculates a void fraction based on the potential difference detected by the voltage measuring section.

According to these method and configuration, the potential difference between the surface of the vibration pipe and the inner surface of the flow section changes according to the void fraction of the two-phase flow flowing therebetween, and therefore, a void fraction can be found by measuring this potential difference.

Effect of the Invention

According to the two-phase flow exciting force evaluation method of the present invention, by measuring the void fraction of a two-phase flow and measuring displacement or stress of the tube body, using one of the tube bodies to be vibrated, it is possible, with a simple configuration, to easily and accurately evaluate the exciting force acting from the two-phase flow on the tube body.

Moreover, according to the two-phase flow exciting force evaluation device of the present invention, by measuring the void fraction of a two-phase flow and measuring displacement or stress of the tube body, using one of the tube bodies to be vibrated, it is possible, with a simple configuration, to easily and accurately evaluate the exciting force acting from the two-phase flow on the tube body.

BEST MODE FOR CARRYING OUT THE INVENTION (First Embodiment)

Hereunder, a first embodiment of the present invention is described, with reference to FIG. 1 through FIG. 4.

Figure 1:
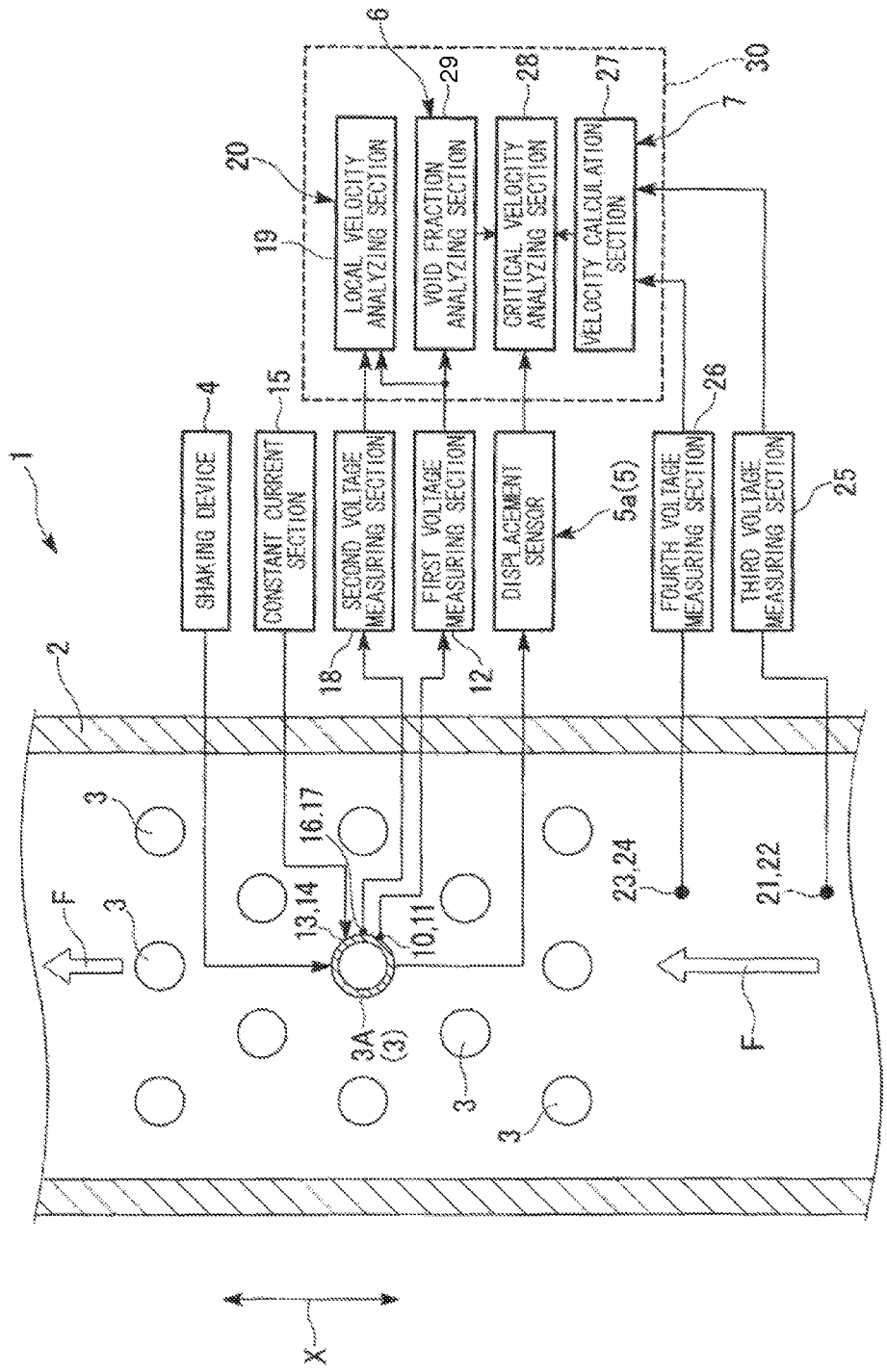
FIG. 1 is a schematic diagram of a two-phase flow exciting force evaluation device of a first embodiment of the present invention.
Figure 2:
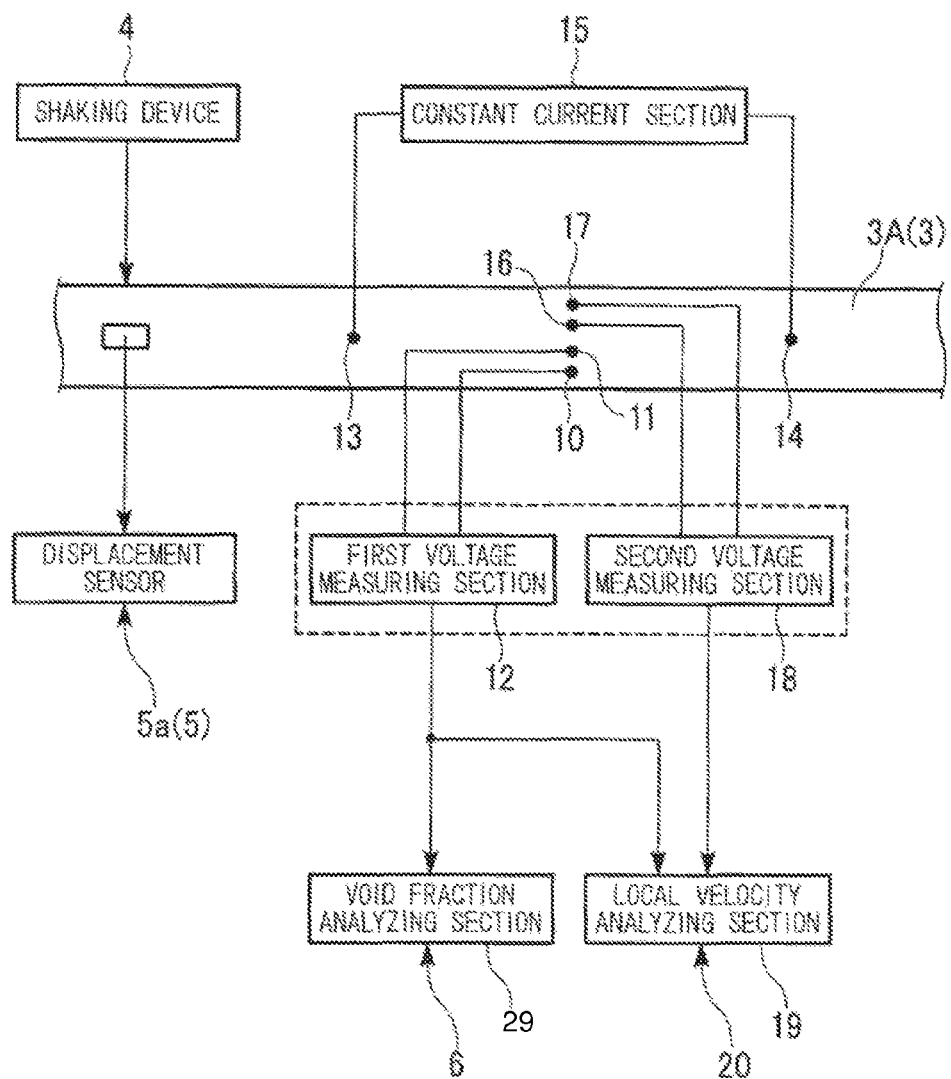
FIG. 2 is a schematic diagram showing details of a vibration pipe of the two-phase flow exciting force evaluation device of the first embodiment of the present invention.
Figure 3:
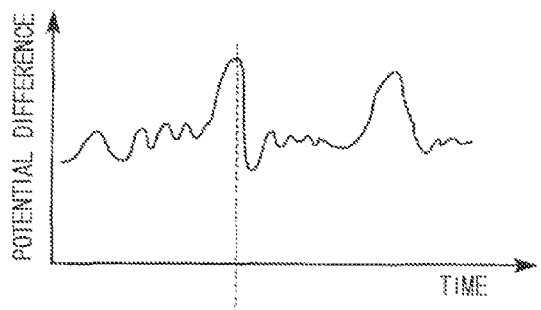
FIG. 3 includes graphs showing potential differences measured by a first voltage measuring section and a second voltage measuring section in the two-phase flow exciting force evaluation device of the first embodiment of the present invention.
Figure 3:
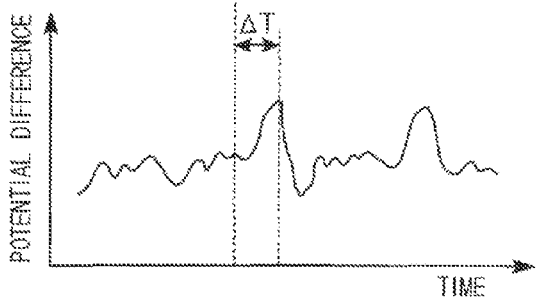

As shown in FIG. 1 and FIG. 2, a two-phase flow exciting force evaluation device 1 of the present embodiment is provided with; a flow section 2 that passes therethrough a two-phase flow F taken as a model flow, a plurality of tube bodies 3 arranged inside the flow section 2 so as to orthogonally intersect with a flow direction X of the two-phase flow F, a shaking device 4 that vibrates the tube bodies 3, an exciting force evaluation device 5 that measures displacement of the tube bodies 3 that are vibrating, a void fraction measuring device 6 that measures the void fraction of the two-phase flow F, and a two-phase flow velocity measuring device 7 that measures the velocity V of the two-phase flow F.

The two-phase flow F is a model flow of a secondary coolant which is boiling in an evaporator, and it is composed of an alcohol and a sulfur hexafluoride gas. Although it is omitted in FIG. 1 and FIG. 2, on the upstream side in the flow direction X, there is provided a supply section which receives supply of the liquid and gas which constitute the two-phase flow F. Moreover, as shown in FIG. 1 and FIG. 2, one of the tube bodies 3 is configured as a vibration pipe 3A to be vibrated by the shaking device 4. Furthermore, the other tube bodies 3 may be of a solid body. The vibration pipe 3A is formed from a metallic material capable of conducting electricity. The shaking device 4 comprises, for example, a solenoid, and it is capable of vibrating the vibration pipe 3A at a required amplitude and frequency which simulate vibration received from the fluid flowing inside. Moreover, the exciting force evaluation device 5 comprises a displacement sensor 5a that measures a displacement of the vibration pipe 3A in a direction orthogonal to the extending direction thereof. The vibration pipe 3A vibrates at an amplitude according to the magnitude of the exciting force from the two-phase flow F. Therefore, the exciting force can be accurately evaluated by measuring the vibration amplitude of the vibration pipe 3A using the displacement sensor 5a.

Furthermore, the void fraction measuring device 6 has a pair of first electrodes 10 and 11 which are provided at two points with a clearance therebetween on the surface of the vibration pipe 3A along the flow direction X, a first voltage measuring section 12 that measures a potential difference between the first electrodes 10 and 11 while one of them is taken as a reference, and a void fraction analyzing section 29 that calculates a void fraction based on the potential difference detected by the first voltage measuring section 12. Furthermore, the void fraction measuring device 6 has a pair of terminals 13 and 14 which are provided on the surface of the vibration pipe 3A along the extending direction thereof so as to have the pair of first electrodes 10 and 11 therebetween, and a constant current section 15 for passing a predetermined electric current between the pair of terminals 13 and 14. Therefore, the electric current flowing between the pair of terminals 13 and 14 causes a potential difference to occur between the first electrodes 10 and 11. The potential difference between the first electrodes 10 and 11 measured by the first voltage measuring section 12 differs depending on the void fraction of the two-phase flow F flowing in the vicinity, and therefore, in the void fraction analyzing section 29, the void fraction of the two-phase flow F flowing in the vicinity can be found based on this potential difference.

Moreover, on the surface of the vibration pipe 3A, at downstream side positions different from those of the pair of first electrodes 10 and 11 along the flow direction X of the two-phase flow F, at two points with a clearance therebetween along the flow direction X, there are provided a pair of second electrodes 16 and 17. With a second voltage measuring section 18, a potential difference between the second electrodes 16 and 17 can be measured. Therefore, in the second voltage measuring section 18, the potential difference according to the void fraction of the two-phase flow F flowing in the vicinity is detected. In FIG. 3(a), potential differences measured by the first voltage measuring section 12, and FIG. 3(b) shows potential differences measured by the second voltage measuring section 18. In a local velocity analyzing section 19, the waveform of the potential difference detected by the first voltage measuring section 12, and a time difference $\Delta T$ to be taken as a phase difference from the waveform of the potential difference detected by the second voltage measuring section 18, are extracted.

Here, the positions in which the pair of first electrodes 10 and 11 are provided, and the positions in which the pair of second electrodes 16 and 17 are provided, are in different positions along the flow direction X of the two-phase flow F. Therefore, the two-phase flow F detected by the pair of first electrodes 10 and 11 on the upstream side, is detected, with the time difference $\Delta T$ corresponding to the velocity V thereof, by the pair of second electrodes 16 and 17 on the downstream side. Therefore, the phase difference between the waveform of the potential difference detected by the first voltage measuring section 12 and the waveform of the potential difference detected by the second voltage measuring section 18, is extracted in the local velocity analyzing section 19, and it is possible to find the velocity V of the two-phase flow F flowing in the vicinity, based on the distance between the pair of first electrodes 10 and 11 and the pair of second electrodes 16 and 17. Consequently, a local velocity measuring device 20 that finds a local velocity V1 of the two-phase flow F flowing in the vicinity of the vibration pipe 3A is configured with; the local velocity analyzing section 19, the pair of first electrodes 10 and 11, the first voltage measuring section 12, the pair of second electrodes 16 and 17, the second voltage measuring section 18, the pair of terminals 13 and 14, and the constant current section 15.

Moreover, the two-phase flow exciting force evaluation device 1 has: a pair of third electrodes 21 and 22 and a pair of fourth electrodes 23 and 24 provided on the upstream side of the group of tube bodies 3 in the flow direction where the pair of third electrodes 21 and 22 and the pair of fourth electrodes 23 and 24 are respectively provided in two positions different in the flow direction X, a third voltage measuring section 25 that measures a potential difference which occurs between the pair of third electrodes 21 and 22 in the two-phase flow F, a fourth voltage measuring section 26 that measures a potential difference which occurs between the pair of fourth electrodes 23 and 24 in the two-phase flow F, and the two-phase flow velocity measuring device 7 which is provided with a velocity calculation section 27 that calculates the velocity V of the two-phase flow F based on measurement results respectively from the third voltage measuring section 25 and the fourth voltage measuring section 26. Here, the positions in which the pair of third electrodes 21 and 22 are provided, and the positions in which the pair of fourth electrodes 23 and 24 are provided, are in different positions along the flow direction X of the two-phase flow F. Therefore, the two-phase flow F detected by the pair of third electrodes 21 and 22 on the upstream side, is detected, with the time difference corresponding to the velocity V thereof, by the pair of fourth electrodes 23 and 24 on the downstream side. Therefore, the phase difference between the waveform of the potential difference detected by the third voltage measuring section 25 and the waveform of the potential difference detected by the fourth voltage measuring section 26, is extracted in the velocity calculation section 27, and it is possible to find an average velocity V of the two-phase flow F flowing in the flow section 2, based on the distance between the pair of third electrodes 21 and 22 and the pair of fourth electrodes 23 and 24.

Figure 4:
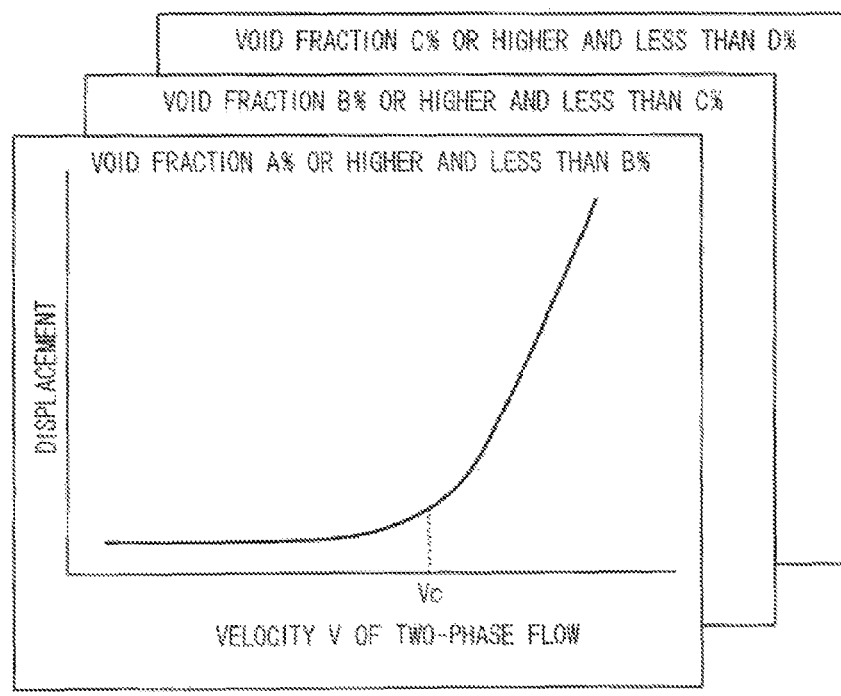
FIG. 4 is a graph showing a relationship between displacement of the vibration pipe and the velocity of the two-phase flow analyzed by a critical velocity analyzing section in the two-phase flow exciting force evaluation device of the first embodiment of the present invention.

Furthermore, the velocity V of the two-phase flow F obtained in the two-phase flow velocity measuring device 7, the displacement of the vibration pipe 3A measured in the exciting force evaluation device 5, and the void fraction of the two-phase flow F obtained in the void fraction measuring device 6 are input to a critical velocity analyzing section 28. The critical velocity analyzing section 28 plots a relationship between the displacement of the vibration pipe 3A and the velocity of the two-phase flow F corresponding to each other, and it finds a critical velocity Vc based on the correlative relationship therebetween. Here, as shown in FIG. 4, the critical velocity analyzing section 28 is capable of finding a critical velocity Vc for each void fraction segment, by plotting, for the input of each void fraction segment of the two-phase flow F, the relationship between the displacement of the vibration pipe 3A and the velocity V of the two-phase flow F. In the present embodiment, the void fraction analyzing section 29 in the void fraction measuring device 6, the local velocity analyzing section 19 in the local velocity measuring device 20, the velocity calculation section 27 in the two-phase flow velocity measuring device 7, and the critical velocity analyzing section 28, are integrally configured as an analyzing device 30.

Next, a two-phase flow exciting force evaluation method in this embodiment is described.

First, as shown in FIG. 1 and FIG. 2, a two-phase flow F taken as a model flow is flowed in the flow section 2, and the vibration pipe 3A, which is one of the tube bodies 3 arranged so as to intersect with the flow of the two-phase flow F, is vibrated by the shaking device 4. As a result, the vibration pipe 3A is excited by an exciting force which acts from the two-phase flow F flowing therearound. The displacement associated with the vibration of the vibration pipe 3A is measured by the exciting force evaluation device 5, and the void fraction measuring device 6 measures the void fraction of the two-phase flow F which is flowing in the vicinity at this time. Moreover, a local velocity V1 is measured by the local velocity measuring device 20. The velocity V of the two-phase flow F supplied into the flow section 2 is measured by the two-phase flow F measuring device. As shown in FIG. 4, the critical velocity analyzing section 28 finds a critical velocity Vc for each void fraction segment.

Here, the void fraction of the two-phase flow F and the exciting force acting on the tube body 3 can both be integrally measured without having to measure them respectively with independent equipment, by conducting the measurement with use of the vibration pipe 3A formed from a conductive metallic material. Therefore, installation of the device can be easily performed with a minimum number of members and a simple configuration, without making the entire device large, and an exciting force and a void fraction can be associated with each other and can be accurately measured. As a result, it is possible, with a simple configuration, to easily and accurately evaluate the exciting force which acts on the tube body 3 from the two-phase flow F. Moreover, in the present embodiment, the local velocity measuring device 20 also correspondingly finds the local velocity V1 of the two-phase flow F flowing in the vicinity of the vibration pipe 3A, and it is thereby possible to also evaluate the relationship between the local velocity V1 and the exciting force.

(Second Embodiment)

Figure 5:
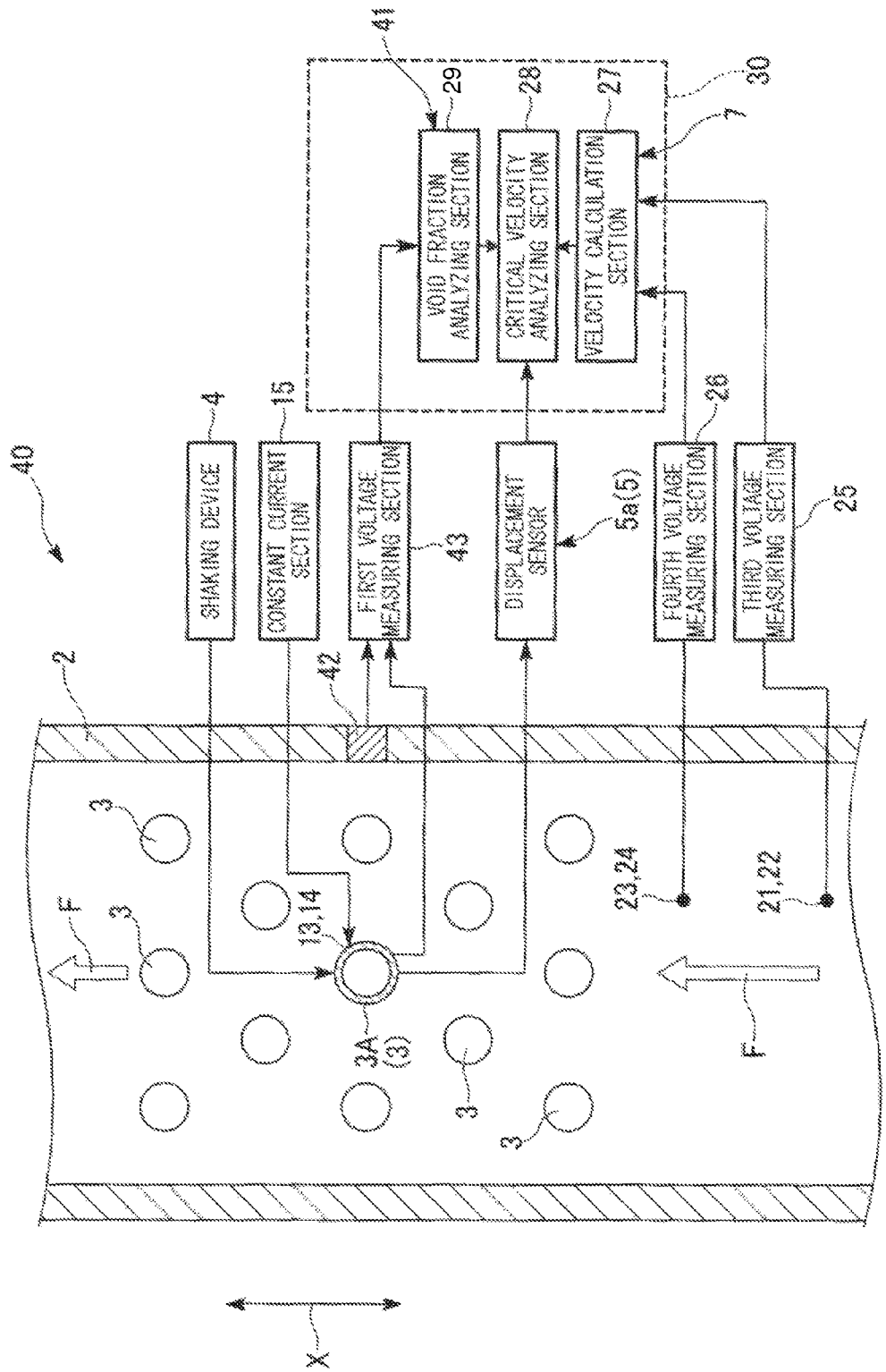
FIG. 5 is a schematic diagram of a two-phase flow exciting force evaluation device of a second embodiment of the present invention.

Next, a second embodiment of the present invention is described. FIG. 5 shows the second embodiment of the present invention. In this embodiment, members which are commonly used in the embodiment described above are given the same reference symbols, and descriptions thereof are omitted.

As shown in FIG. 5, in a two-phase flow exciting force evaluation device 40 of the present embodiment, a void fraction measuring device 41 has; a first voltage measuring section 43 that measures a potential difference between first electrodes 42 provided on the inner surface of the flow section 2 facing the vibration pipe 3A and the surface of the vibration pipe 3A, and a void fraction analyzing section 29 that calculates a void fraction based on the potential difference detected by the first voltage measuring section 43.

Also in this type of two-phase flow exciting force evaluation device 40, the Potential difference between the first electrodes 42 and the vibration pipe 3A changes according to the void fraction of the two-phase flow F flowing between the first electrodes 42 and the vibration pipe 3A. Therefore it is possible, in the void fraction analyzing section 29, to calculate and find a void fraction based on the potential difference measured by the first voltage measuring section 43. As a result, also in the present embodiment, it is possible, with a simple configuration, to easily and accurately evaluate the exciting force acting from the two-phase flow on the vibration pipe 3A, based on this void fraction, using the vibration pipe 3A, which is formed from a conductive metallic material.

The embodiments of the present invention have been described in detail with reference to the drawings. However, specific configurations are not limited by these embodiments, and various design modifications may be made without departing from the scope of the present invention.

In the respective embodiments above, in the exciting force evaluation device 5, displacement of the vibration pipe 3A is measured using the displacement sensor 5a, and the exciting force is evaluated according to this displacement. However, it is not limited to this. For example, a stress sensor may be provided on the vibration pipe 3A, and the exciting force may be evaluated according to the stress detected by this stress sensor. Furthermore, in the vibration pipe 3A, which is vibrated and displaced by the exciting force, the stress also changes according to the displacement, and accordingly, the exciting force can also be evaluated by extracting the amplitude of the stress waveform. Moreover, in the respective embodiments above, the vibration pipe 3A is formed from a conductive metallic material. However, it is sufficient that the surface of the vibration pipe 3A is at least partially formed from an electrically conductive metallic material.

Furthermore, in the above embodiments, evaluation of the exciting force of the two-phase flow is described to be conducted with use the two-phase flow exciting force evaluation device 1 or 40, however, it is not limited to this. In evaluating the exciting force of the two-phase flow, it is sufficient if there is provided a configuration in which; at least one of the plurality of tube bodies 3 is vibrated by the shaking device 4 to measure the displacement or stress of the tube body corresponding to the exciting force acting on the tube body which is vibrating, and a potential difference between the electric potential at a predetermined position on the surface of the tube body 3 and a reference electric potential can be measured.

Description of Reference Symbols 1, 40 Two-phase flow exciting force evaluation device
2 Flow section
3 Tube body
3A Vibration pipe
4 Shaking device
5 Exciting force evaluation device
6, 41 Void fraction measuring device
7 Two-phase flow velocity measuring device
10, 11, 42 First electrode
12, 43 First voltage measuring section
29 Void fraction analyzing section
16, 17 Second electrode
18 Second voltage measuring section
19 Local velocity analyzing section
20 Local velocity measuring device
28 Critical velocity analyzing section

The invention claimed is:

1. A two-phase flow exciting force evaluation method for evaluating an exciting force which acts, from a two-phase flow flowing in a flow section, on a plurality of tube bodies arranged orthogonally in the flow section so as to intersect with the flow of the two-phase flow, comprising:
    forming a surface of one of the plurality of tube bodies at least partially from a conductive material;
    measuring displacement or stress of the tube body in a state of being vibrated by a shaking device; and
    measuring each void fraction of the two-phase flow flowing in the vicinity of the tube body, based on a potential difference between an electric potential at a predetermined position on the surface of the tube body, and a reference electric potential.

2. A two-phase flow exciting force evaluation method according to claim 1, further comprising:
    measuring a velocity of the two-phase flow; and
    finding a critical velocity for each of the void fraction, based on the measured void fraction and the velocity of the two-phase flow, and on the displacement or stress of the tube body.

3. A two-phase flow exciting force evaluation method according to claim 2, wherein,
    the void fraction of the two-phase flow is found by measuring a potential difference between two points on the surface of the tube body.

4. A two-phase flow exciting force evaluation method according to claim 3, wherein,
    on the surface of the tube body, a potential difference between another two points in different positions along the flow direction of the two-phase flow is further measured, and
    a local velocity of the two-phase flow which flows in the vicinity of the tube body is found based on a phase difference of waveforms of potential difference measured respectively at both of the two points.

5. A two-phase flow exciting force evaluation method according to claim 1, wherein
    the void fraction of the two-phase flow is found by measuring a potential difference between two points on the surface of the tube body.

6. A two-phase flow exciting force evaluation method according to claim 5, wherein,
    on the surface of the tube body, a potential difference between another two points in different positions along the flow direction of the two-phase flow is further measured, and
    a local velocity of the two-phase flow which flows in the vicinity of the tube body is found based on a phase difference of waveforms of potential difference measured respectively at both of the two points.

7. A two-phase flow exciting force evaluation method according to claim 1, wherein,
    the void fraction of the two-phase flow is found by measuring a potential difference between the surface of the tube body and the inner surface of the flow section.

8. A two-phase flow exciting force evaluation device for evaluating an exciting force which acts, from a two-phase flow flowing in a flow section, on a plurality of tube bodies arranged orthogonally in the flow section so as to intersect with the flow of the two-phase flow, comprising:
    a vibration pipe which is configured as one of the plurality of tube bodies, and a surface of which is at least partially formed from a conductive material;
    a shaking device that vibrates the vibration pipe;
    an exciting force evaluation device that measures displacement or stress of the vibration pipe; and
    a void fraction measuring device that measures each void fraction of the two-phase flow flowing in the vicinity of the vibration pipe, based on a potential difference between an electric potential at a predetermined position on the surface of the vibration pipe, and a reference electric potential.

9. A two-phase flow exciting force evaluation device according to claim 8, further comprising:
    a two-phase flow velocity measuring device that measures a velocity of the two-phase flow.

10. A two-phase flow exciting force evaluation device according to claim 9, further comprising:
    a critical velocity analyzing section that finds a critical velocity for each of the void fraction, based on the velocity of the two-phase flow measured by the two-phase flow velocity measuring device, the void fraction of the two-phase flow measured by the void fraction measuring device, and the displacement or stress of the vibration pipe measured by the exciting force evaluation device.

11. A two-phase flow exciting force evaluation device according to claim 10, further comprising:
    a pair of first electrodes which are provided with a clearance therebetween on the surface of the vibration pipe, and
    a first voltage measuring section that detects a potential difference between the pair of first electrodes,
    wherein the void fraction measuring device having a void fraction analyzing section that calculates a void fraction based on the potential difference detected by the first voltage measuring section.

12. A two-phase flow exciting force evaluation device according to claim 11, further comprising:
    a pair of second electrodes, with a clearance therebetween, are provided on the surface of the vibration pipe, at positions different in the flow direction of the two-phase flow from those of the pair of first electrodes, a local velocity measuring device that communicates with the first voltage measuring section that detects the potential difference between the pair of first electrodes and a second voltage measuring section that detects a potential difference between the pair of second electrodes, a local velocity analyzing section that finds a local velocity of the two-phase flow flowing in the vicinity of the vibration pipe, based on a waveform phase difference of the potential difference detected by the first voltage measuring section and a waveform phase difference of the potential difference detected by the second voltage measuring section.

13. A two-phase flow exciting force evaluation device according to claim 9, further comprising:

a pair of first electrodes which are provided with a clearance therebetween on the surface of the vibration pipe, and a first voltage measuring section that detects a potential difference between the pair of first electrodes, wherein the void fraction measuring device having a void fraction analyzing section that calculates a void fraction based on the potential difference detected by the first voltage measuring section.

14. A two-phase flow exciting force evaluation device according to claim 13, further comprising:

a pair of second electrodes, with a clearance therebetween, are provided on the surface of the vibration pipe, at positions different in the flow direction of the two-phase flow from those of the pair of first electrodes, a local velocity measuring device that communicates with the first voltage measuring section that detects the potential difference between the pair of first electrodes and a second voltage measuring section that detects a potential difference between the pair of second electrodes, and a local velocity analyzing section that finds a local velocity of the two-phase flow flowing in the vicinity of the vibration pipe, based on a waveform phase difference of the potential difference detected by the first voltage measuring section and a waveform phase difference of the potential difference detected by the second voltage measuring section.

15. A two-phase flow exciting force evaluation device according to claim 8, further comprising:

a pair of first electrodes which are provided with a clearance therebetween on the surface of the vibration pipe, and a first voltage measuring section that detects a potential difference between the pair of first electrodes, wherein the void fraction measuring device having a void fraction analyzing section that calculates a void fraction based on the potential difference detected by the first voltage measuring section.

16. A two-phase flow exciting force evaluation device according to claim 15, further comprising:

a pair of second electrodes, with a clearance therebetween, are provided on the surface of the vibration pipe, at positions different in the flow direction of the two-phase flow from those of the pair of first electrodes, a local velocity measuring device that communicates with the first voltage measuring section that detects the potential difference between the pair of first electrodes and a second voltage measuring section that detects a potential difference between the pair of second electrodes, and a local velocity analyzing section that finds a local velocity of the two-phase flow flowing in the vicinity of the vibration pipe, based on a waveform phase difference of the potential difference detected by the first voltage measuring section and a waveform phase difference of the potential difference detected by the second voltage measuring section.

17. A two-phase flow exciting force evaluation device according claim 8, further comprising:

an electrode provided on the inner surface of the flow section so as to face the surface of the vibration pipe, and a voltage measuring section that detects a potential difference between the vibration pipe and the electrode, wherein the void fraction measuring device having a void fraction analyzing section that calculates a void fraction based on the potential difference detected by the voltage measuring section.

* * * * *